(12) United States Patent  
Wildman

(10) Patent No.: US 7,828,549 B1
(45) Date of Patent: Nov. 9, 2010

(54) LINGUAL SELF-LIGATING ORTHODONTIC BRACKET, AND METHODS FOR MAKING AND USING THE SAME

(75) Inventor: Alexander J. Wildman, The Woodlands, TX (US)

(73) Assignee: WIOS, LLC, The Woodlands, TX (US)

( * ) Notice: Subject to any disclaimer, the term of this patent is extended or adjusted under 35 U.S.C. 154(b) by 2 days.

(21) Appl. No.: 12/256,859

(22) Filed: Oct. 23, 2008

Related U.S. Application Data

(60) Provisional application No. 60/984,312, filed on Oct. 31, 2007.

(51) Int. Cl.
*A61C 3/00* (2006.01)
(52) U.S. Cl. ............................................ 433/10; 433/11
(58) Field of Classification Search ................. 433/8–17
See application file for complete search history.

(56) References Cited

U.S. PATENT DOCUMENTS

| | | | |
|---|---|---|---|
| 678,453 | A | 7/1901 | Angle |
| 1,552,413 | A | 9/1925 | Angle |
| 1,584,501 | A | 5/1926 | Angle |
| 1,821,171 | A | 9/1931 | Atkinson |
| 1,952,320 | A | 3/1934 | Johnson |
| 2,011,575 | A | 8/1935 | Ford |
| 2,023,849 | A | 12/1935 | McCoy |
| 2,196,516 | A | 4/1940 | Atkinson |
| 2,305,916 | A | 12/1942 | Atkinson |
| 2,406,527 | A | 8/1946 | Berke |
| 2,665,480 | A | 1/1954 | Johnson |
| 2,671,964 | A | 3/1954 | Russell et al. |
| 2,705,367 | A | 4/1955 | Berke |
| 2,759,265 | A | 8/1956 | Johnson |
| 3,123,553 | A | 3/1964 | Abrams |
| 3,193,930 | A | 7/1965 | Bien |
| 3,302,288 | A | 2/1967 | Tepper |
| 3,477,128 | A | 11/1969 | Andrews |
| 3,593,421 | A | 7/1971 | Brader |
| 3,660,900 | A | 5/1972 | Andrews |
| 3,748,740 | A | 7/1973 | Wildman |
| 3,775,850 | A | 12/1973 | Northcutt |
| 3,780,437 | A | 12/1973 | Wildman |
| 3,842,503 | A | 10/1974 | Wildman |
| 3,854,207 | A | 12/1974 | Wildman |

(Continued)

*Primary Examiner*—Cris L Rodriguez
*Assistant Examiner*—Matthew M Nelson
(74) *Attorney, Agent, or Firm*—Marger Johnson & McCollom, P.C.

(57) ABSTRACT

A self-ligating orthodontic bracket system is provided, comprising a bracket to be mounted on the lingual side of the tooth and a self-ligating insert. The insert comprises a retention arm and a lockarm pivotally engaged together. The retention arm includes: a retention spring; a topside arm; and a pivot ring connecting the retention spring to the topside arm. The lockarm includes: an attachment portion having a pivot bar configured to be received in the pivot ring of the retention arm; a strut portion connected to the attachment portion; and a clasp portion having a clasp lock and an unlocking opening. The clasp lock is configured to engage a chokebox stem of the bracket. A retention groove in the bracket retains the retention arm of the insert. The bracket includes slots for occlusal, edgewise and gingival archwires. A method of providing orthodontic treatment and an orthodontic system are also provided.

14 Claims, 9 Drawing Sheets

U.S. PATENT DOCUMENTS

| | | |
|---|---|---|
| 4,337,037 A | 6/1982 | Kurz |
| 4,382,782 A | 5/1983 | Klein et al. |
| 4,386,908 A | 6/1983 | Kurz |
| 4,443,187 A | 4/1984 | Shaftner et al. |
| 4,443,189 A | 4/1984 | Wildman |
| 4,484,931 A | 11/1984 | Kushigian |
| 4,669,981 A | 6/1987 | Kurz |
| 5,791,897 A | 8/1998 | Wildman |
| 5,906,486 A * | 5/1999 | Hanson ............ 433/11 |
| 6,485,299 B1 * | 11/2002 | Wildman ............ 433/10 |
| 6,932,597 B2 * | 8/2005 | Abels et al. ............ 433/10 |

* cited by examiner

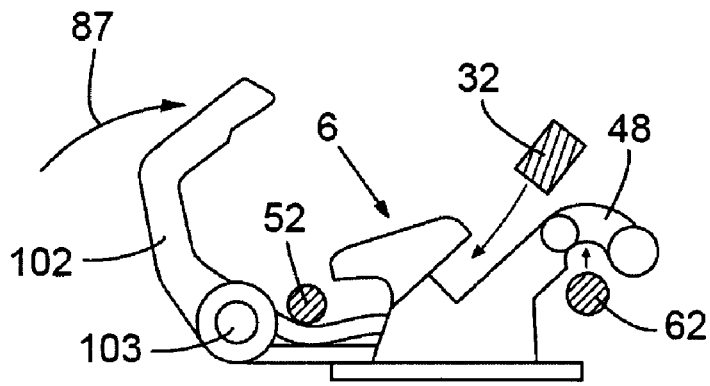
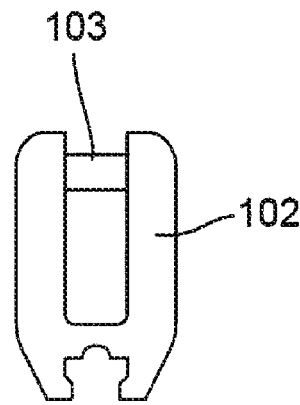
FIG. 16
FIG. 17
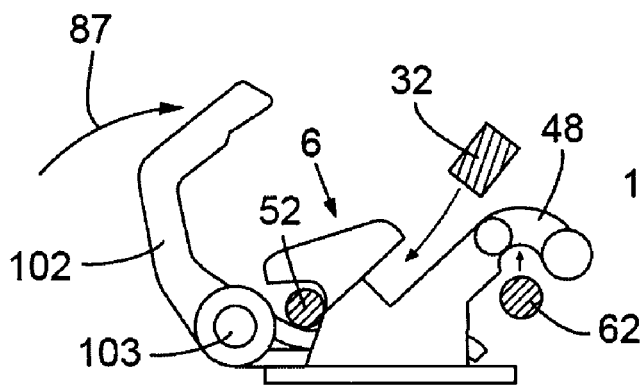
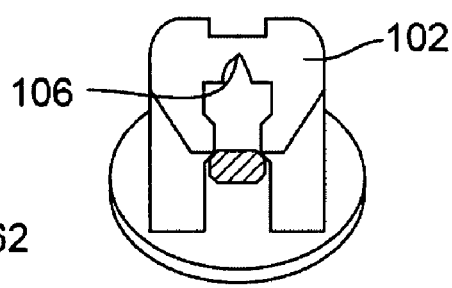
FIG. 18
FIG. 19
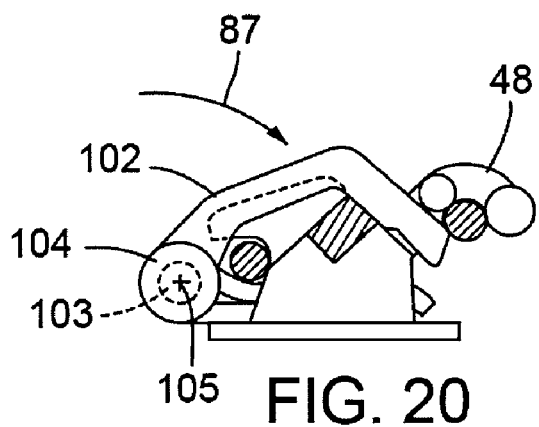
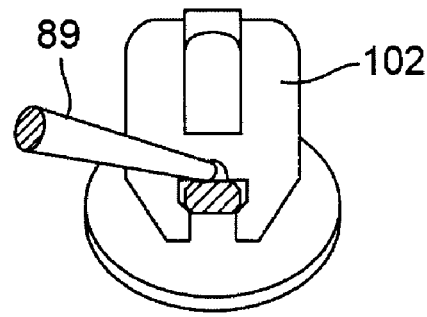
FIG. 20
FIG. 21

LINGUAL SELF-LIGATING ORTHODONTIC BRACKET, AND METHODS FOR MAKING AND USING THE SAME

RELATED APPLICATION DATA

This application claims benefit of U.S. provisional patent application Ser. No. 60/984,312, filed Oct. 31, 2007, titled SELF-LIGATING ORTHODONTIC BRACKET, AND METHODS FOR MAKING AND USING THE SAME, the contents of which are herein incorporated by reference in their entirety.

BACKGROUND

1. Technical Field

The present invention relates generally to methods and apparatus for orthodontic treatment. In another aspect, the present invention relates to methods of making and using the archwire bracket force delivery system, more commonly referred to as orthodontic braces or orthodontic appliances. In particular, the present invention relates to the conversion of the known labial art to lingual applications as well as original concepts designed to meet the unique demands of the lingual environment.

2. Description of the Related Labial Art

Generally, orthodontic treatment of the teeth is accomplished by applying force to the teeth with a series of archwires positioned in and across a number of brackets. Since the beginning of orthodontics, in the late 1800's, orthodontists have been pursuing the goals of increased appliance resiliency, control, comfort to the patient, and easier manipulation for the doctor.

Edward H. Angle is considered the father of modern orthodontics. Angle's U.S. Pat. No. 678,453 discloses a rigid outer archwire with teeth tied to the archwire to draw them into position. The bands on the teeth were attachments that were really simple cleats. In 1925, in U.S. Pat. No. 1,584,501, Angle added a rectangular slot to the bracket with wings to receive tiewires. Because the slot was perpendicular to the long axis of the tooth it was called the Edgewise Appliance. The initial heavy gold archwire was bent to the shape of the malocclusion and was gradually straightened out. The device produced very precise control but was extremely rigid and non-resilient. To provide increased resiliency the sequential use of a number of single archwires, beginning with relatively small diameter round wires, and finishing with large rectangular wires, was incorporated in the Edgewise technique. Angle's Edgewise bracket has evolved into the Edgewise technique that is in common use today.

Typically, the archwire was secured in the archwire slot using wire ligatures twisted around the wings extending laterally on opposite sides of the slot. The use of elastomer O-rings in place of the wire ligatures was described by Anderson and Klein in U.S. Pat. No. 4,382,782. The use of elastomers was a definite step forward in the Edgewise technique. By their very nature, the elastomers provided a gentler and longer acting force. They were softer and were easier to install. However, the elastomer O-rings did have one problem; they absorbed water and lost some of their elastic force over time, necessitating replacement of the O rings.

Also, in 1925, Angle was issued U.S. Pat. No. 1,552,413, which disclosed a bracket designed to receive a rectangular archwire that was called a ribbon arch because the long axis of the archwire cross section was in the same plane as the long axis of the tooth. This bracket was locked with a pin which was held in place by bending the pin after it was inserted in the locking position. This bracket was later used by Spencer Atkinson and was developed into what was known as the Universal Technique. Atkinson's art was taught in U.S. Pat. Nos. 1,821,171; 2,196,516; and 2,305,916. Wildman, in U.S. Pat. No. 3,854,207, offered a self-ligating version of the Universal Technique in 1974.

J. W. Ford, in 1933 in U.S. Pat. No. 2,011,575, described a sleeve and tube unit that was probably the first self-ligating lingual bracket. The locking device was a friction lock.

McCoy presented a different approach that still used the gold arch technology. McCoy's bracket was simply a gold tube opened up to allow a snap fit to securely hold an appropriate round arch. A wide variety of torquing spurs were soldered to the arch. The gold arch allowed a full range of movement. These early efforts produced some very nice cases, even by modern standards, but the process was very demanding and time consuming. McCoy described the details of this process in U.S. Pat. No. 2,023,849. This patent was in the same year as the Ford patent. Because McCoy lectured showing treated cases, some people call McCoy the originator of self-ligating brackets.

The ribbon arch bracket was modified by Dr. P. R. Begg and was used extensively in what was known as the Begg technique. The Begg technique was well-received because it produced gentle forces which made it easy to start a case. It fell out of favor though because it was difficult to adequately finish cases. Begg's modification is described in U.S. Pat. No. 3,123,553 and used the pin groove of the Angle ribbon arch to attach a wide variety of torquing and rotational auxiliaries. In some iterations, Begg used a secondary archwire to provide torque control. Coordinating all these complex torque vectors made finishing cases difficult and led to the demise of the Begg technique.

To further increase the resiliency of the archwires, orthodontists began incorporating all sorts of geometric bends in almost every conceivable shape. An extreme example of this approach is described by Brader in U.S. Pat. No. 3,593,421. The downside of this was the difficulty of putting precise bends in the archwire. These archwires became too flimsy to control, and were eventually abandoned.

To provide increased resiliency and still maintain control, orthodontists sometimes turned to multiple archwires. J. D. Berke, in U.S. Pat. Nos. 2,406,527 and 2,705,367, described a bracket which is essentially a button with two channels separated by the body of the bracket. The two archwires were connected by rigid connectors between two teeth. In one configuration connectors were fixed and in another configuration they were slidable. This was the first mention of slidable, rigid interarch connectors. The archwire was connected to the tooth by pulling the two archwires away from each other and snapping the two archwires over the tooth. The archwires, returning to shape, moved the tooth into the proper position by seating the archwires in the archwire slot. The rigid sliding connectors helped in manipulation of the archwires but the rigid construction made this system difficult to use. Thus, this bracket was never produced in any significant quantities commercially.

Another approach was described by Joseph Johnson in U.S. Pat. Nos. 1,952,320; 2,665,480; and 2,759,265. Johnson incorporated two small diameter archwires held together in a ribbon arch configuration with the long axis going through the two wires parallel to the long axis of the tooth. This twin wire did produce increased resiliency but placing any compensating bends was impossible. This was a friction lock.

In 1952 Russell described in U.S. Pat. No. 2,671,964, a two piece unit that closed off the slot locking in twin wires as proposed by Johnson.

In 1965, S. M. Bien, in U.S. Pat. No. 3,193,930, proposed an interesting approach using one, two or three separated archwires. The channels that accepted the archwires were in the shape of V's and did not provide an edgewise slot.

U.S. Pat. No. 3,302,288 to Teppler discloses a similar two wire bracket arrangement using parallel spaced crossbars interconnected by a rigid member. Since this interarch connector was rigid it made this arrangement difficult to use. The archwires cannot be pulled apart easily to allow insertion and release.

Another attempt at attaining precision with two wires was described by Northcott in U.S. Pat. No. 3,775,850. Northcott connected two and three archwires together with interarch connectors. These connectors were rigid cast or brazed metal, both fixed and slidable. This rigid system was tied into the corresponding slots in the labial bracket. The sliding rigid connectors had to be tied in with twisted steel ligatures, however.

The problem with all of the two-wire techniques is the difficulty in putting in compensating bends. In theory, if the bracket of the tooth is put on the tooth in such a position that the channel of the bracket is in an ideal position, a straight archwire placed in this channel would produce a tooth positioned in the ideal position. In actual practice this does not happen, though. To compensate for the fact that this is not an ideal position the orthodontist had to make compensating bends in the archwire. Compensating bends in even a single archwire are difficult and time consuming for the orthodontist.

This problem was addressed by Dr. Larry Andrews using methods described in U.S. Pat. Nos. 3,477,128 and 3,660,900. Andrews attempted to position the slots in the bracket in such a relation to the base of the bracket that was applied to the tooth so that the slot assumed an ideal position in the average tooth. Since the brackets were generally put on the tooth by the orthodontist in the mouth using the orthodontist's trained eye, errors in position were inevitable. Also, not all teeth are average, and this also increases errors. So, the orthodontist must still finish cases with compensating bends. This is much easier with Andrews' straight arch system. Putting compensating bends in two wires is, from a practical point of view, impossible.

3. Description of the Related Lingual Art

Dr. A. J. Wildman's U.S. Pat. No. 3,842,503 in 1974 was the beginning of what is called lingual orthodontics. Wildman stated in this patent—"The archwires may be mounted on the lingual side of the teeth as well as the labial side, as previously done. This is possible because brackets may be secured directly to the teeth without bands. Thus, for cosmetic reasons or otherwise, it may be desired to mount a lingual archwire". He also introduced the concept of cutting teeth off of a model of the teeth and placing them in an ideal position. The brackets could then be placed on the models and the resulting set-up could act as a means of making an ideal archwire. The brackets could then be transferred to the mouth in the ideal position by a variety of means, and the archwire could then be tied into the brackets on the teeth. This would produce an ideal position for the teeth. This technique was later refined and called the Class System.

This patent ('503) suggested using cast gold bases as a means of indexing. The brackets were brazed to the bases in a perfect position. The castings and brackets were then transferred to the teeth and cemented or bonded in place just as a gold inlay would be seated.

Wildman has previously developed lingual orthodontic methods and brackets as described in U.S. Pat. Nos. 3,748,740, which was a self-ligating Begg bracket; 3,780,437, which was the production version of the Edgelok bracket; 3,842,503, which described for the first time the concept of "lingual orthodontics" and the concept of the Class System; 3,854,207, which was a self ligating version of the Universal System; 4,443,187; 4,484,931, which was a method of bonding using burnished index tabs; and U.S. Pat. No. 4,443,189, which was a lingual bracket which locked in a second or auxiliary archwire. This lingual bracket was called "The Kelly Bracket" after the first patient it was tried upon. These concepts were a good start but needed further development.

In U.S. Pat. Nos. 4,337,037, 4,386,908, and 4,669,981 (1982, 1983 and 1987 respectively), Kurz described a series of shapes that he felt fit best on the lingual anatomical surfaces of the teeth. These shapes were incorporated in brackets that had to be tied either with steel ligatures or with elastomer O's. The steel wires were very sharp and uncomfortable to the patient. When plastic O's were used it was often necessary to use a double tie arrangement, with O rings doubled back on themselves in order to apply enough force from the O ring to properly seat the archwire. Orthodontists complained that this method was difficult and inefficient.

U.S. Pat. No. 6,485,299 to Wildman describes an insert configured to convert a non-self-ligating lingual bracket into a self-ligating bracket. The insert is removably attachable to the non-self-ligating lingual bracket and includes a self-ligating mechanism. According to a preferred embodiment, the bracket insert includes a pin, a tube, and a lock arm. The pin is configured to be removably secured to the non-self-ligating bracket. The tube is attached to or formed from an occlusal end of the retention pin. The lockarm is partially mounted within the tube and is capable of rotation between a ligating and non-ligating position. In its ligating position the lockarm securely retains an archwire within the archwire slot of the non-self-ligating bracket using detents in the rotating lockarm that snap into corresponding architecture in the body. This approach works very well but it does not lock an occlusal auxiliary archwire. An interarch connector between the two wires opens up all sorts of opportunities.

Thus, there is a need for an improvement in the arrangement described in the above patent. Ideally, the body would have an auxiliary slot that would allow insertion from the incisal direction. There would also be a typical edgewise slot that would allow insertion from the lingual direction. In U.S. Pat. No. 5,791,897, FIGS. 33-40B and the accompanying description explain the virtues of the occlusal auxiliary archwire and the edgewise archwire used together as a working arch. Another improvement would be the ability to use an edgewise archwire alone to add any necessary compensating bends.

The orthodontic profession needs a lingual self-ligating bracket that could lock in a single, light occlusal archwire to begin the unraveling of teeth in the first phase of treatment. In this system, an edgewise archwire would complement the occlusal archwire to provide ideal control of roots in all planes of space. A third, gingival archwire could be used to provide additional control. Further, a single archwire could be used in the edgewise slot to provide the fine finishing details. Many combinations expressing the needs of various techniques could be met with this arrangement. Accordingly, a need remains for a multiple archwire bracket that overcomes the deficiencies in the prior art.

SUMMARY

The present invention provides a self-ligating orthodontic bracket system, composed of a bracket to be mounted on the lingual side of the tooth and a self-ligating insert. The first object of the present invention is the use of the lockable, occlusal archwire inserted from the incisal direction, and the use of a lockable edgewise archwire inserted parallel to the occlusal plane. The occlusal archwire would preferably be a light, round NiTi wire, which would be used to control gross rotations and to begin the leveling process. The occlusal locking mechanism would be opened up to allow insertion of the edgewise wire to provide precise root control. In this half-lock position the edgewise wire could be removed and adjusted without interference, because the occlusal wire is still locked in place in the half-lock position. Preferably, in most cases, once the occlusal wire is placed, it would not be removed for the duration of the treatment.

The two archwire system can handle most orthodontic situations well. The present invention also allows for use of a third, gingival archwire for additional flexibility and control.

BRIEF DESCRIPTION OF THE DRAWINGS

The above and other objects, features and advantages of the disclosure will be more clearly understood from the following detailed description taken in conjunction with the accompanying drawings, in which:

FIG. 16 is a side view of a body pad ligating assembly in the open position showing the occlusal archwire, the edgewise archwire and the gingival archwire positioned to be inserted into their respective slots in accordance with a third embodiment of the invention;

FIG. 17 is a plan view of the lockarm of FIG. 16.

FIG. 18 is a side elevation view of the body pad ligating assembly of FIG. 16 with the self-ligating insert in the half-lock position and the gingival archwire snapped into the gingival archwire snap-groove in accordance with the third embodiment of the invention, the archwires shown in cross section;

FIG. 19 is a gingival end elevation view of the body pad ligating assembly of FIG. 18 in the half-lock position;

FIG. 20 is a side view of the body pad ligating assembly of FIGS. 16-19 with the self-ligating insert in the locked position locking the occlusal archwire and the edgewise archwire in place in their slots, and the gingival archwire snap-locked in the gingival snap-groove in accordance with the third embodiment of the invention.

FIG. 21 is a gingival end elevation view of the body pad ligating assembly and a release tool inserted into the release notch to open the lockarm in accordance with the third embodiment of the invention;

DETAILED DESCRIPTION

Figure 1A:
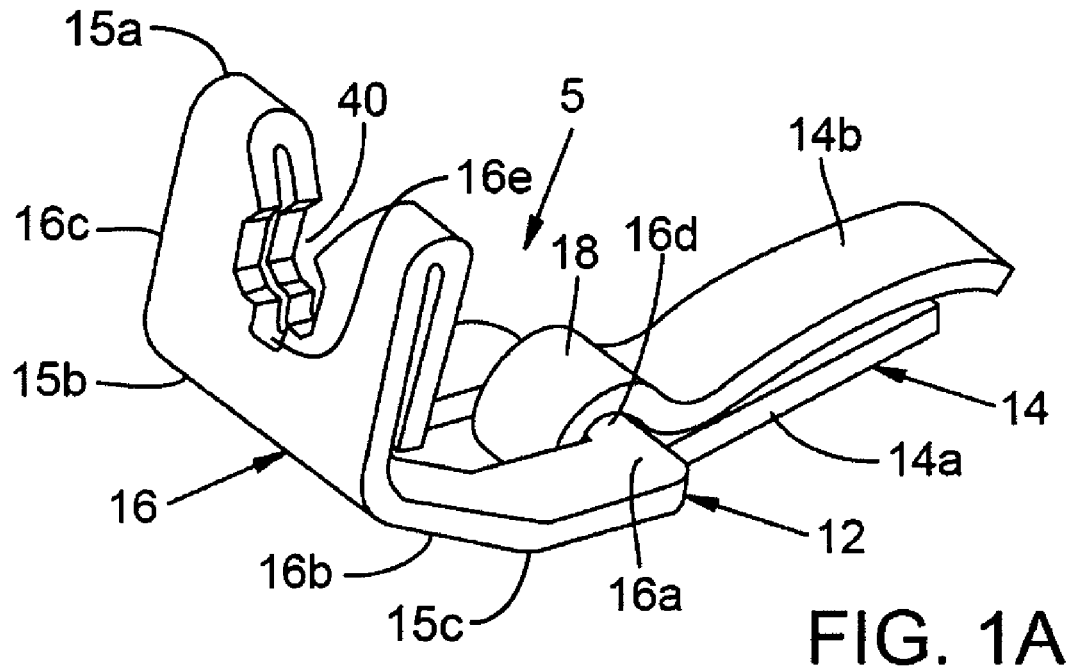
FIG. 1A is a perspective view of a self-ligating insert in accordance with a first embodiment of the invention.

Example embodiments of the invention are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will fully convey the scope of the disclosure to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one skilled in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1B:
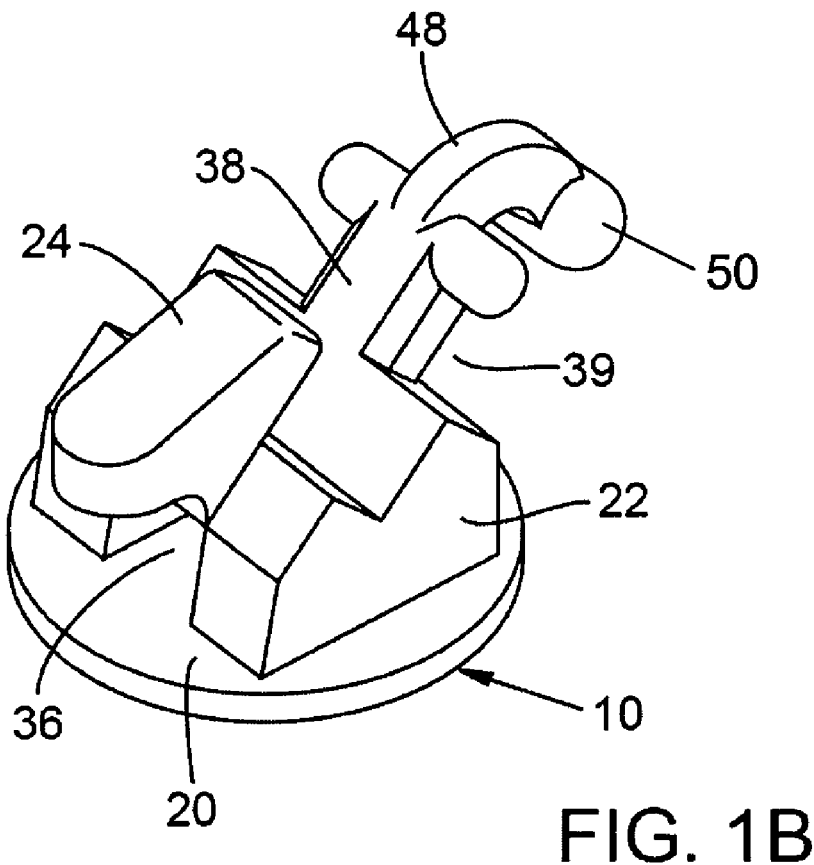
FIG. 1B is a perspective view of a bracket in accordance with the first embodiment of the invention.
Figure 1C:
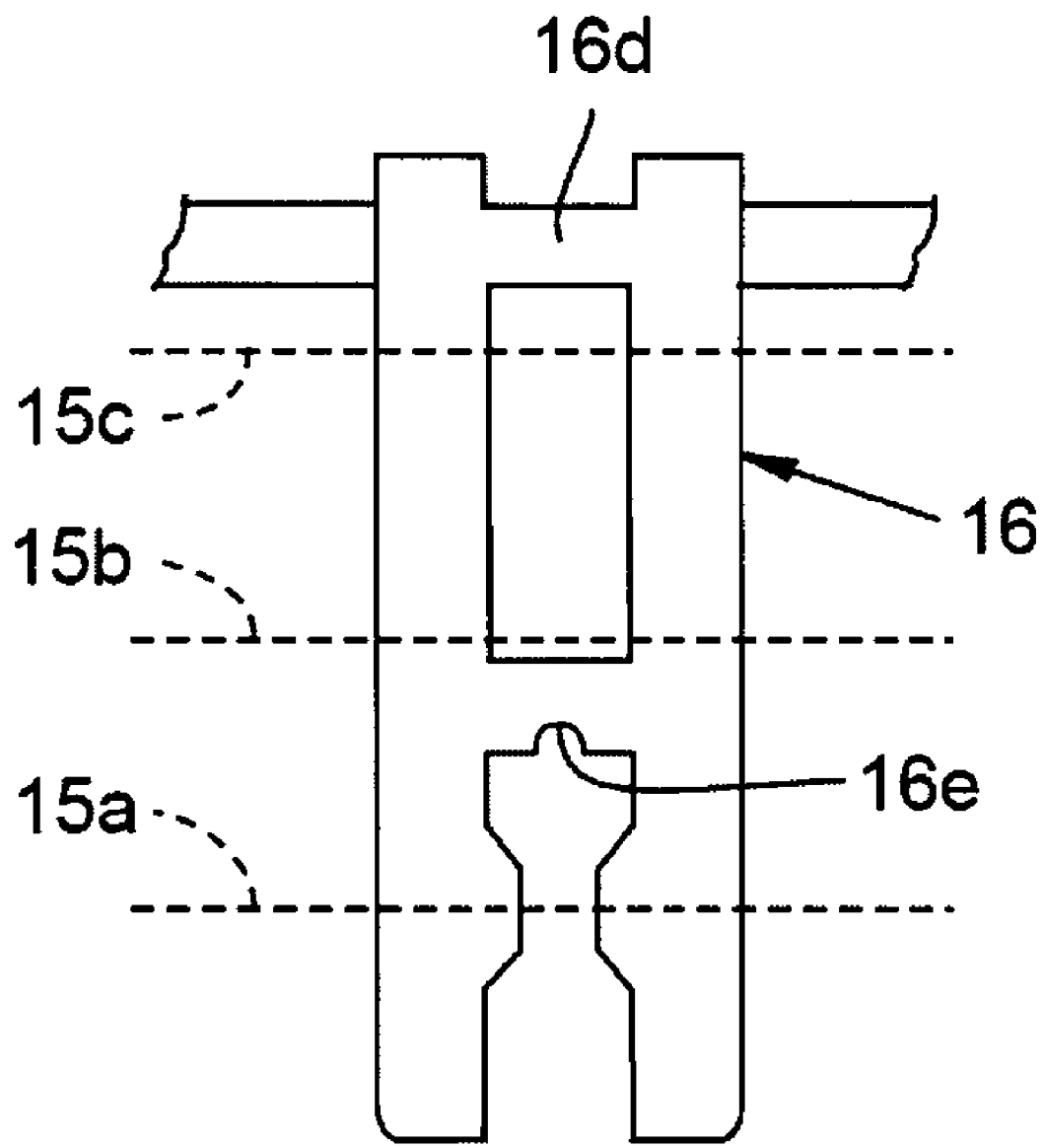
FIG. 1C is a plan view of a lock arm prior to shaping in accordance with the first embodiment of the invention.

FIGS. 1A through 13 illustrate the construction and operation of a lingual self-ligating bracket system in accordance with a first embodiment of the invention. Referring to FIGS. 1A-1C, the lingual self-ligating bracket system includes a bracket 10 which is shown in FIG. 1B and a self-ligating insert 5 which is shown in FIG. 1A. The self-ligating insert 5 consists of two main parts: a retention arm 14 and a lockarm 16. The retention arm 14 includes a retention spring 14a, a topside arm 14b, and a pivot ring 18 which, when assembled, holds a pivot bar 16d. The lockarm 16 is formed by three bends folding up the flat shape shown in FIG. 1C. Bend 15a forms the clasp lock 40 which will engage the chokebox stem 38 when the self-ligating insert 5 is in the full lock position. This will securely lock an edgewise archwire and an occlusal archwire in place. The second bend 15b and the third bend 15c allow the lockarm 16 to conform to the shape of the bracket body 22. Following the three bends, the lockarm 16 will include an attachment portion 16a, a strut portion 16b, and a clasp portion 16c. The attachment portion 16a includes the pivot bar 16d. The clasp portion 16c includes the clasp lock 40 and an unlocking slot 16e. The bracket 10 includes a pad 20 and a bracket body 22. The bracket body 22 includes a gingival hook 50, a chokebox 39, a chokebox stem 38 with perpendicular projections 44 on opposite lateral sides, topside head 24, a curved hook stem 48, and a retention groove 36.

Figure 2:
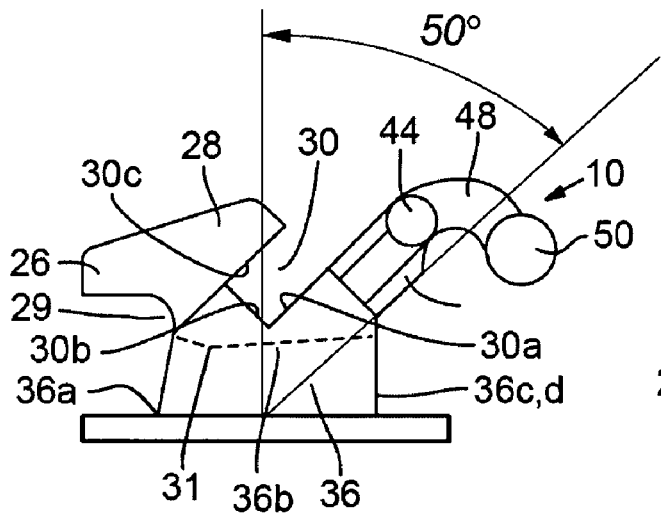
FIG. 2 is a side elevation view of a body pad ligating assembly in accordance with the first embodiment of the invention.
Figure 4:
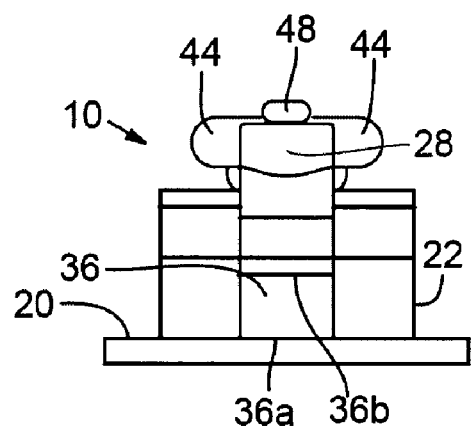
FIG. 4 is an incisal end elevation view of the body pad ligating assembly of FIGS. 2 and 3 showing the incisal surface.
Figure 3:
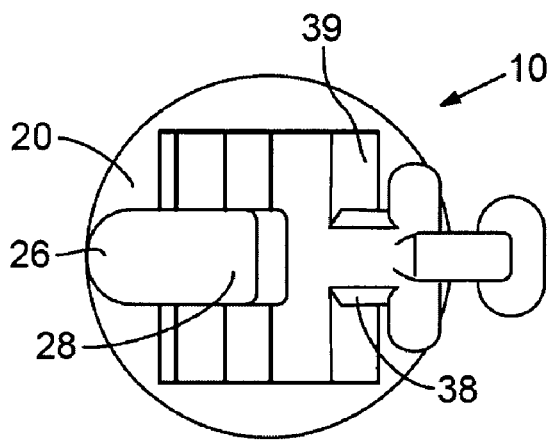
FIG. 3 is a plan view of the body pad ligating assembly of FIG. 2.
Figure 5:
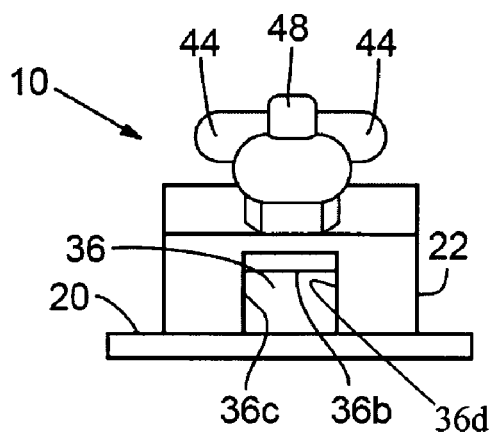
FIG. 5 is a gingival end elevation view of the body pad ligating assembly of FIGS. 2 and 3 showing the gingival surface.

FIG. 2 shows a cross-sectional midline view of the retention groove 36 which is enclosed by brazing the bracket body 22 to the pad 20. This construction forms the flat pad base 36a of the retention groove 36 and the irregular topside 36b of the retention groove 36. The side walls 36c and 36d of the retention groove 36 are formed when the body 22 of the bracket 10 is brazed to the pad 20. The side walls 36c and 36d of the retention groove 36 are parallel and equidistant from each other. The topside wall 36b of the retention groove 36 begins with an incisal opening (as shown in FIG. 4). The top wall of the retention groove 36 inclines sharply in a gingival direction toward an apex that forms a pressure point 31 or constriction. The top wall of the retention groove 36 then extends gradually gingivally to form a gingival opening of the retention groove 36 (as shown in FIG. 5). The incisal and gingival openings of the retention groove 36 are substantially identical in shape. The bracket 10 also includes an edgewise slot 30, configured to receive an edgewise archwire 32, an occlusal slot 29, configured to receive an occlusal archwire 52, and a gingival slot 91, configured to receive a gingival archwire 62 (see FIG. 6). As shown in FIG. 2, the angle of the edgewise slot 30 is about 50 degrees. In other words, the angle of the edgewise slot 30 with respect to a vector normal to the surface of the pad 20 is approximately 50 degrees.

Figure 7:
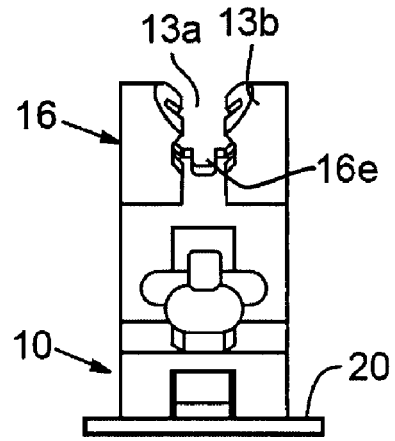
FIG. 7 is a gingival end elevation view of the body pad ligating assembly in the open position.
Figure 8:
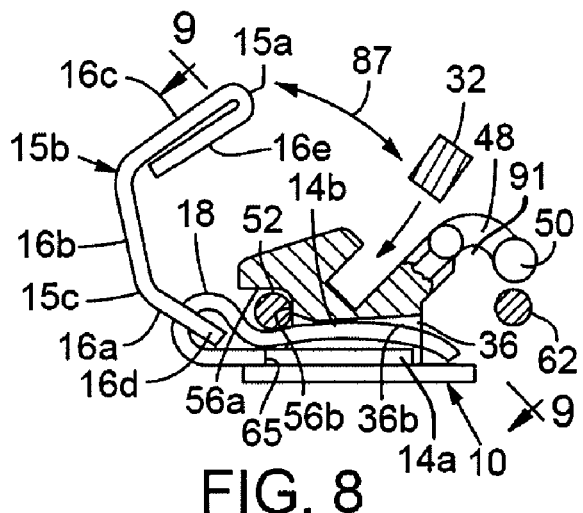
FIG. 8 is a side elevation view of the body pad ligating assembly of FIGS. 2 and 3 with the self-ligating insert in the half-lock position.
Figure 9:
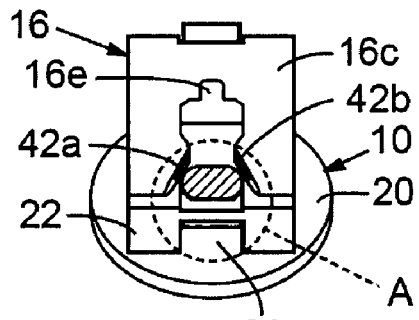
FIG. 9 is a gingival end elevation view of the body pad ligating assembly of FIG. 8 in the half-lock position.
Figure 10:
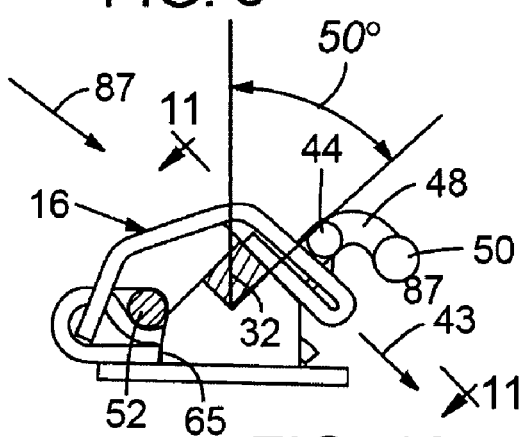
FIG. 10 is a side elevation view of the body pad ligating assembly of FIG. 8 with the self-ligating insert in the locked position locking in the occlusal and the edgewise archwires in their corresponding slots.
Figure 11:
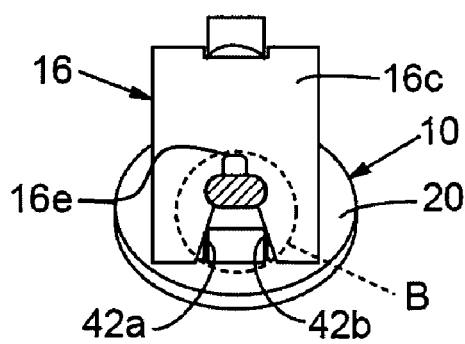
FIG. 11 is a gingival end elevation view of the body pad ligating assembly of FIG. 10 showing the lock arm locked into the locking stem of the body.

The self-ligating insert 5 is assembled by sliding the lockarm 16 into the pivot ring 18 of the retention arm 14. This is accomplished by mechanically spreading the retention spring 14a and the top side arm 14b wide enough to insert the incisal pivot bar 16d into the pivot ring 18. When the mechanical spreading tool is released the pivot ring 18 will place a compressive force on the pivot bar 16d. This allows the lockarm 16 to pivot within the confines of the pivot ring 18. The center of rotation will be the center of the pivot ring 18 as shown in side views (FIGS. 6, 8, and 10) and in gingival elevation views (FIGS. 7, 9 and 11).

The lingual self-ligating bracket system is then assembled by inserting the retention arm 14 of the self-ligating insert 5 into the retention groove 36 of the bracket 10. The retention spring 14a and top side arm 14b fit compressively into the retention groove 36 of the bracket 10 where they are kept in place by the pressure point 31. As the retention spring 14a and top side arm 14b first enter the retention groove 36 they reach a position of maximum retention which is called the lock open position.

Figure 6:
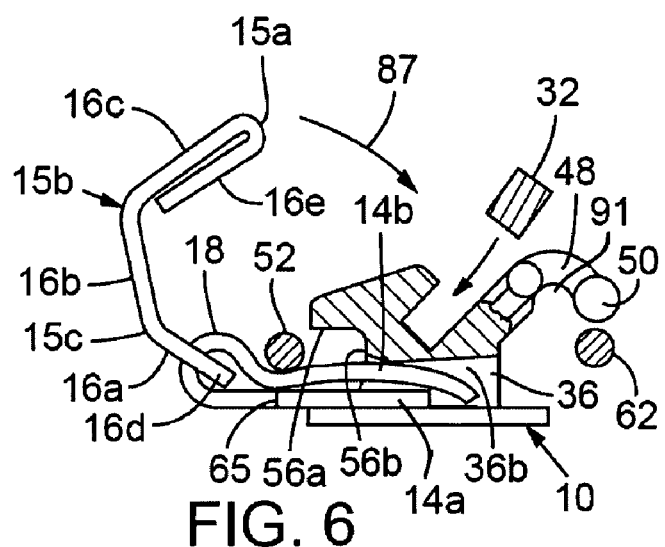
FIG. 6 is a cross-section view of the body pad ligating assembly of FIGS. 2 and 3 in the open position showing the occlusal archwire and the edgewise archwire positioned to be inserted into their respective slots.
Figure 9A:
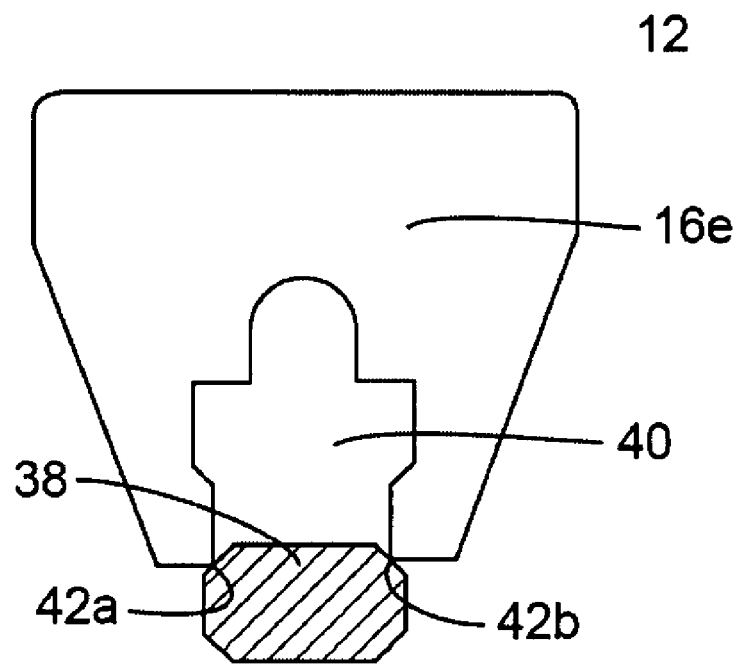
FIG. 9A is a detailed view of portion A of FIG. 9, showing that, as forces continue along vector 87, the locking clasps will begin to be forced from the lock open to the lock closed position.
Figure 11A:
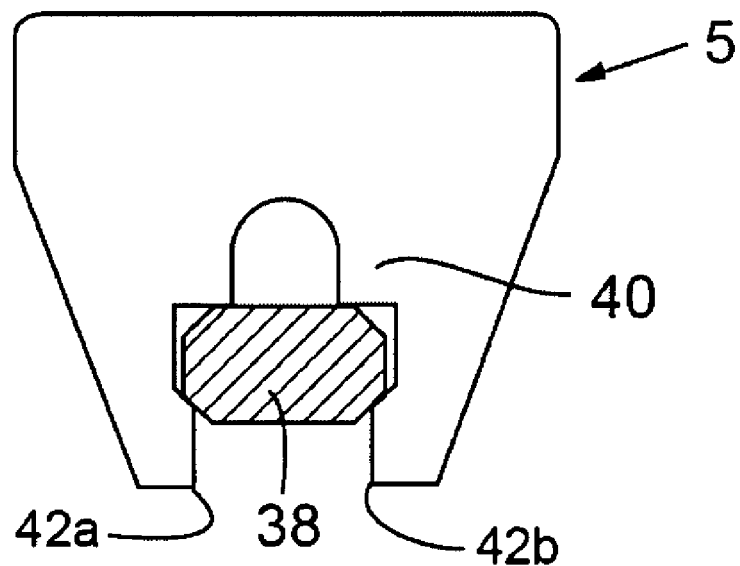
FIG. 11A is a detailed view of portion B of FIG. 11.

When the retention arm 14 is partially inserted into the retention channel 36, it assumes the lock open position shown in FIG. 6. FIG. 6 also shows the occlusal archwire 52 and the edgewise archwire 32 being placed in the occlusal slot 29 and the edgewise slot 30, respectively. As seating pressure along the vector 87 is applied by the operator, the lockarm 16 begins to engage the edgewise archwire 32 and to collect the occlusal wire 52 into a half-locked position as shown in FIG. 8. Continued force along the seating vector 87 locks both archwires 32 and 52 as shown in FIG. 10. In other words, the lockarm 16 pivots from a lock open position shown in FIGS. 6 and 7 to the half-lock position shown in FIGS. 8, 9, and 9a. If pressure of the seating vector 87 is maintained in a clockwise manner the lockarm 16 will lock into the chokebox stem 38 beneath projections 44 as shown in FIGS. 10, 11, and 11a. When the lockarm 16 is snapped into place it produces a very strong seating mechanism and thus the occlusal archwire 52 and the edgewise archwire 32 are securely locked in place (as shown in FIGS. 10, 11 and 11a).

In actual practice the edgewise archwire 32 may not be placed at the beginning of treatment. In a typical approach, orthodontists could lock in a light, resilient occlusal archwire 52 initially that would begin the unraveling of rotations. The orthodontist then could add a second edgewise archwire 32 in the next phase of treatment. The occlusal archwire 52, preferably round, could be made of soft, resilient Ni—Ti wire. This would allow the orthodontist to begin the case with gentle forces on the teeth.

The use of the occlusal archwire 52 and the edgewise archwire 32 together provides control of the roots in the working stage of treatment. The occlusal archwire 52 and the edgewise archwire 32 can be connected using interarch connectors. U.S. Pat. No. 5,791,897 describes the various forms and uses of interarch connectors.

A gingival slot 91, as shown in FIG. 6, may be used to receive a third gingival archwire 62. This could be used primarily with various interarch connectors that call for three archwire configurations.

According to embodiments of the invention, the strong chewing forces which the patient sometimes inflicts upon the lingual self-ligating bracket system will not unlock it. Finger pressure will not unlock the lockarm 16 either. However, the unlocking opening 16e is provided such that an adequate instrument, such as a scaler or an explorer, can be placed in the unlocking opening 16e. Then, a gentle prying motion is all that is necessary to open the lockarm 16. This is also shown in FIG. 21.

Figure 12:
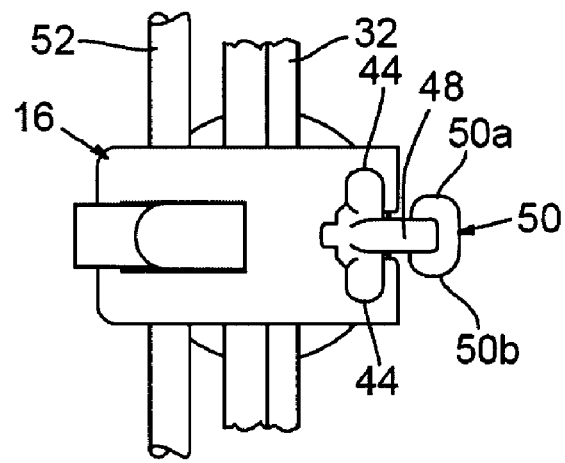
FIG. 12 is a plan view of the body pad ligating assembly of FIG. 10 showing a round occlusal archwire and an edgewise archwire locked into the occlusal and edgewise slots.
Figure 13:
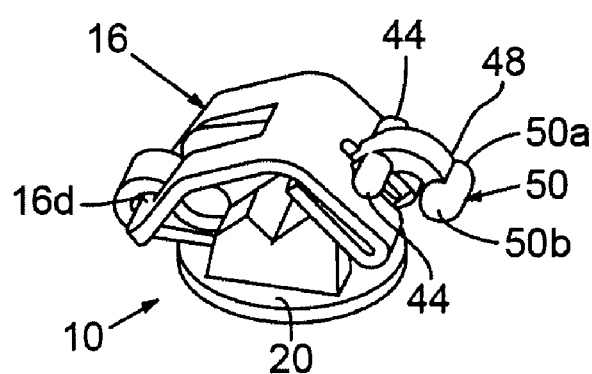
FIG. 13 is a perspective view of the self-ligating insert of FIG. 10 locked into the bracket shown with the archwires removed.

FIG. 12 is a plan view of the lingual self-ligating bracket system showing an incisal round archwire 52 and an edgewise archwire 32 locked into the occlusal and edgewise slots 29 and 30, respectively. The gingival hook 50 includes two rounded protrusions 50a and 50b. The gingival hook 50 is connected to the bracket 10 by the curved hook stem 48. FIG. 13 is a perspective view showing the lockarm 16 locked into the choke box 39 of the bracket 10. For illustration purposes, the archwires 32 and 52 have been removed from the system in the view of FIG. 13.

Figure 14A:
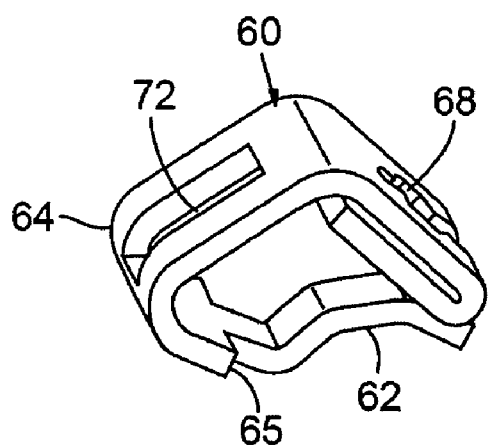
FIG. 14A is a perspective view showing a one piece retention arm-lockarm unit, in accordance with a second embodiment of the invention.
Figure 14B:
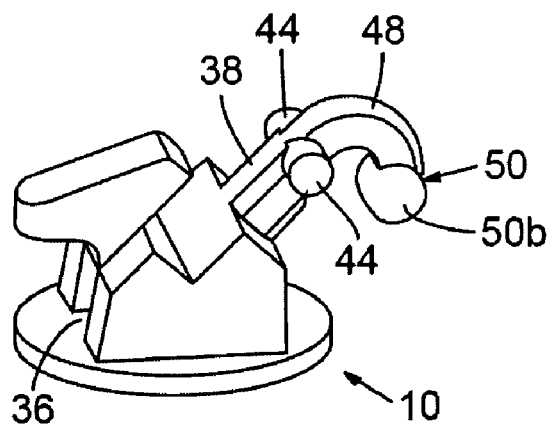
FIG. 14B is a perspective view of a bracket body in accordance with the second embodiment of the invention.
Figure 15:
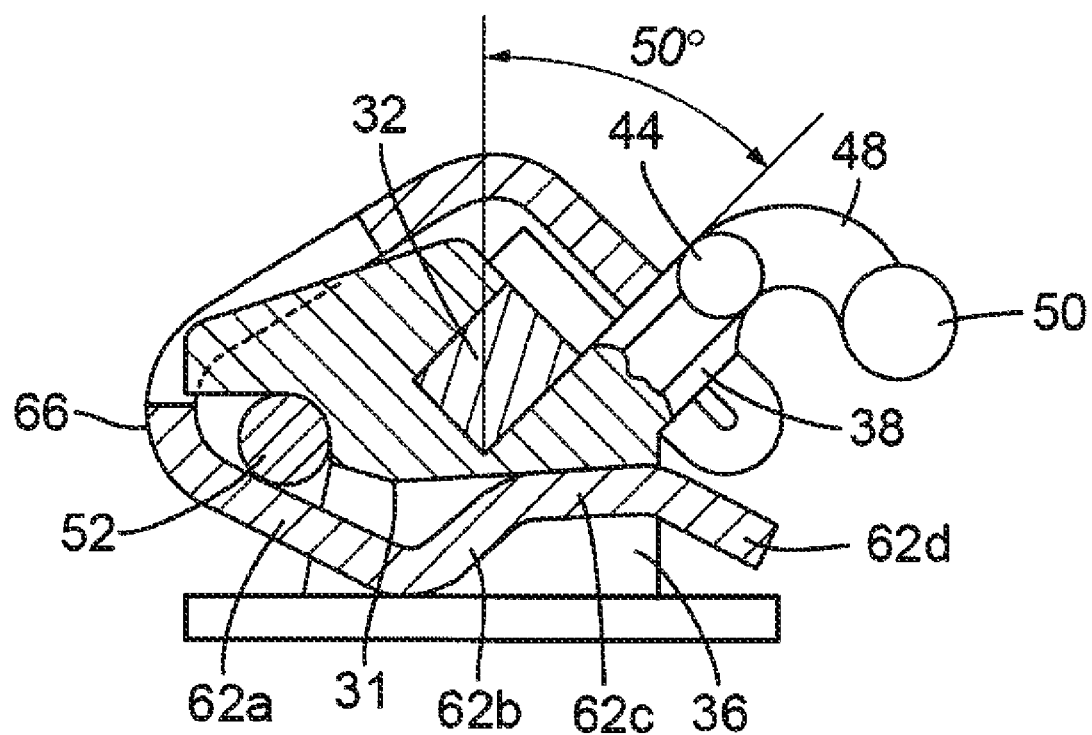
FIG. 15 is a cross-sectional view of a one piece retention arm-lockarm unit of FIG. 14A locking an occlusal archwire and an edgewise archwire into the occlusal and edgewise slots of the bracket body of FIG. 14B.

FIGS. 14A through 15 illustrate the construction and operation of a lingual self-ligating bracket system in accordance with a second embodiment of the invention.

FIG. 14A is a perspective view showing a one-piece retention arm-lockarm unit 60. The one-piece retention arm-lockarm unit 60 includes a clasp portion 68, for engaging with the chokebox stem 38 of the bracket 10, and a retention portion 62, for engaging with the retention groove 36. The one-piece retention arm-lockarm unit 60 may also include a shoulder 65 configured to aid in positioning of the retention portion 62 in the retention groove 36. The one-piece retention arm-lockarm unit 60 can be folded out of a one piece blank of material which would most desirably be a heat treated stainless steel such as 17/7-condition A. Tooling for this embodiment may be complicated and require a progressive die and perhaps a second operation. Although the tooling may be expensive it might produce a very inexpensive part. FIG. 15 shows this solid self-ligating unit 60 locked into the bracket 10 of FIG. 14B. The bracket 10 of FIG. 14B can be similar to or identical to the bracket 10 of FIG. 1B. As shown in FIG. 15, an occlusal archwire 52 and an edgewise archwire 32 can be locked into place in the bracket 10 using the one-piece retention arm-lockarm unit 60. Also, as shown in FIG. 15, the angle of the edgewise slot 30 can be about 50 degrees.

FIGS. 16 through 23 illustrate the construction and operation of a lingual self-ligating bracket system in accordance with a third embodiment of the invention.

The lingual self-ligating bracket system in accordance with the third embodiment includes a much stronger, rounded, and smoother lockarm 102 formed using Metal Injection Molding (MIM) technology that replaces the stamped lockarm 16 of the first embodiment. The general function and shape is the same, however. In the third embodiment, the same bracket 10 can be used, as shown in FIG. 1B. The same retention arm 14 can also be used and the same general shape and form of the first embodiment can be retained. The locking mechanism should be gentle, but also capable of the necessary precision and strength. Because the lock has a stronger locking action and it moves in a narrower range it should also be much more precise. The MIM process provides the necessary close tolerances to make this possible. The MIM process also provides much greater design flexibility.

FIG. 16 shows the MIM lockarm 102 pivoting around the pivot ring 18 of the retention arm 14. When the lockarm 102 is locked into the chokebox stem 38 the edgewise archwire 32 and the occlusal archwire 52 are securely locked into place. FIG. 16 also illustrates a gingival archwire 62 that can engage with the gingival hook 50.

FIG. 17 is a plan view of the MIM lockarm 102. The flat pivot bar 16d of the first embodiment is replaced by a round molded pivot bar 103 that is molded into the lock arm 102, making a solid part. This is designed to be assembled inside the pivot ring 18 of the retention arm 14. A round bar inside a circular ring provides smoother movement and easier use. The smooth flowing rounded edges are shown in FIGS. 16 thru 21.

The strong chewing forces which the patient sometimes inflicts upon the lingual self-ligating bracket system will not release the lockarm 102. Finger pressure will not unlock the lockarm 102 either. An unlocking opening 106 is provided to release the lockarm 16. An adequate instrument, such as a scaler or explorer, can be placed in the unlocking opening 106. The leverage is such that a gentle prying motion is all that is necessary to open the lockarm 16, as shown in FIG. 21.

Figure 22:
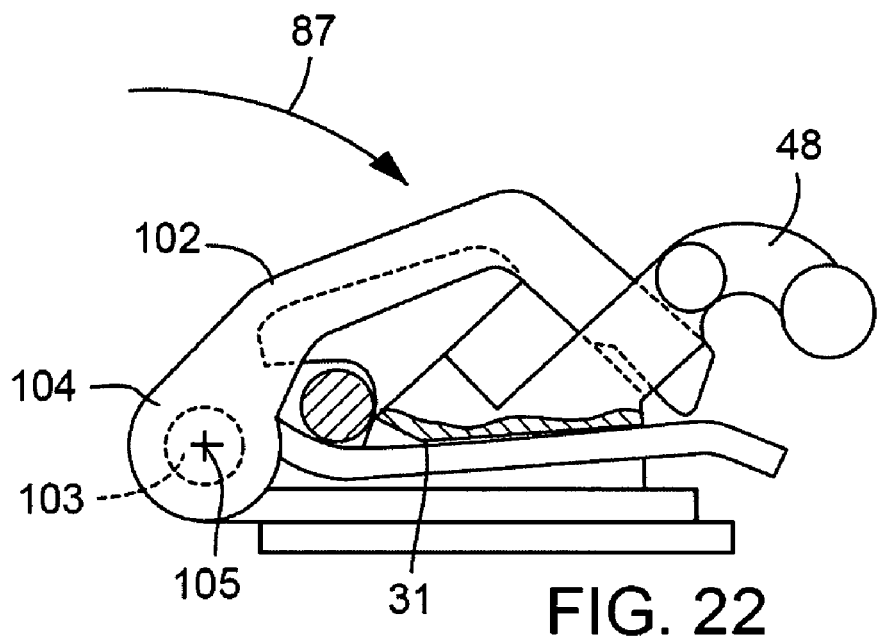
FIG. 22 is a cross-section view of a body pad ligating assembly of FIG. 20 in the closed position.
Figure 23:
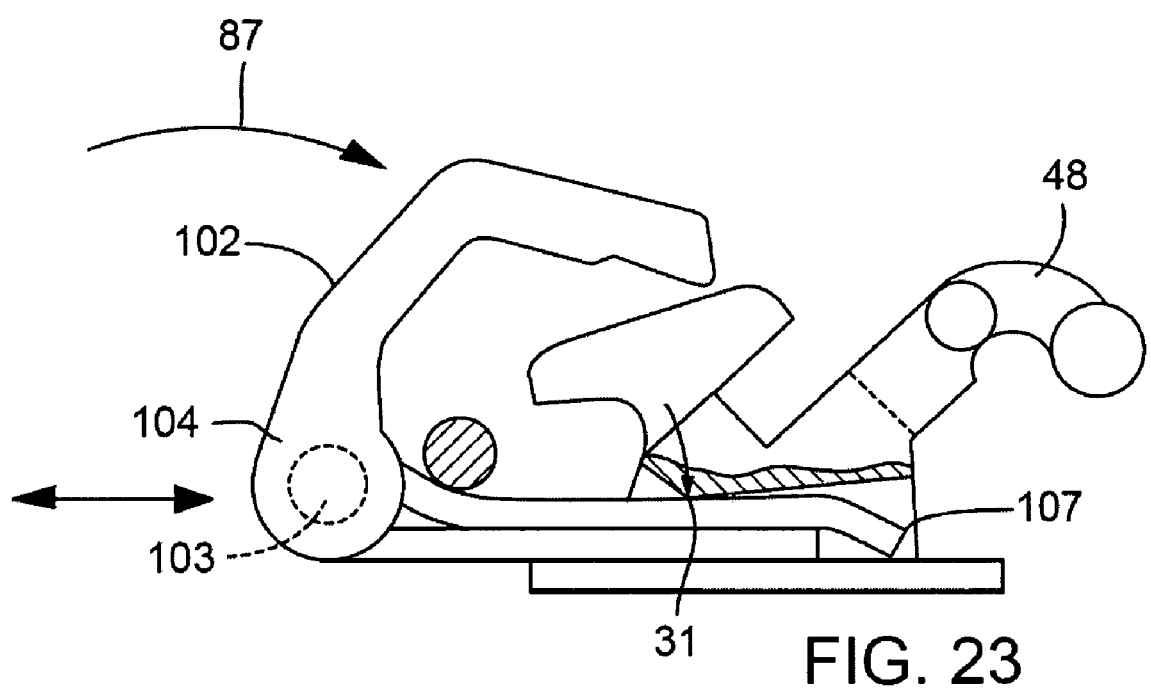
FIG. 23 is a cross-section view of a body pad ligating assembly of FIG. 20 in the half-lock position.

One other feature of the third embodiment is the release lock 107 (see FIG. 23) that keeps the self-ligating insert from sliding into the mouth when the lockarm 102 is in the open position. FIG. 22 shows the lockarm 102 in the closed position such that the retention arm 14 is under gentle compression in the retention groove 36. When the lockarm 102 is open, however, the retention arm 14 is gradually compressed by pressure point 31. Because of the release lock 107, when the lockarm 102 is partially withdrawn from the bracket 10, the retention arm 14 reaches a point where it will not withdraw any farther except under heavy force. This condition is shown in FIG. 23. Thus, the release lock 107 prevents the self-ligating insert from sliding into the mouth when the lockarm 102 is in the open position.

Although the above description has been directed to a single self-ligating insert, one of ordinary skill in the art would appreciate that various self-ligating inserts may be used in order to provide various forces on the archwires. According to embodiments of the invention, these different self-ligating inserts can be used universally with the bracket to accommodate different treatment options.

Some embodiments of the invention have been described above, and in addition, some specific details are shown for purposes of illustrating the inventive principles. However, numerous other arrangements may be devised in accordance with the inventive principles of this patent disclosure. Further, well known processes have not been described in detail in order not to obscure the invention. Thus, while the invention is described in conjunction with the specific embodiments illustrated in the drawings, it is not limited to these embodiments or drawings. Rather, the invention is intended to cover alternatives, modifications, and equivalents that come within the scope and spirit of the inventive principles set out in the appended claims.

I claim:

1. A self-ligating insert, comprising:
    a retention arm, including:
        a retention spring;
        a topside arm having a curved shape along a length of the topside arm such that an end of the topside arm is bent toward the retention spring; and
        a pivot ring connecting the retention spring to the topside arm; and
    a lockarm pivotally engaged with the retention arm, including:
        an attachment portion having a pivot bar configured to be received in the pivot ring of the retention arm;
        a strut portion connected to the attachment portion; and
        a clasp portion having an opening including a clasp lock, at least one protrusion, and an unlocking slot disposed at an end of the opening, wherein the clasp lock has a first width and is configured to engage a chokebox stem of a bracket and wherein the unlocking slot has a second width narrower than the first width.

2. The self-ligating insert of claim 1, wherein the pivot bar has a round cross-section and is molded with the lockarm.

3. The self-ligating insert of claim 1, wherein the retention arm further comprises a release lock disposed at an end portion of the retention arm, the release lock being configured to engage with a wall of a retention groove in the bracket when the lock arm is partially withdrawn from the bracket.

4. A combination self-ligating insert and bracket wherein the bracket comprises:
   a pad;
   a body disposed on the pad, including;
      a curved hook stem extending from the body;
      a gingival hook disposed at an end of the curved hook stem;
      a chokebox stem disposed between the curved hook stem and the body;
      a topside head disposed at an incisal end of the body;
      a retention groove disposed in the body;
      an edgewise slot disposed in the body and configured to receive an edgewise archwire; and
      an occlusal slot disposed under the topside head and configured to receive an occlusal archwire;
      the retention groove including:
      an incisal opening having a first cross-sectional area;
      a gingival opening having a second cross-sectional area; and
      a pressure point between the incisal opening and the gingival opening such that the retention groove has a third cross-sectional area and configured to engage with the retention arm, wherein the third cross-sectional area is smaller than at least one of the first and second cross-sectional areas;
   wherein the self-ligating insert comprises a retention arm configured to engage with the retention groove of the bracket and includes:
      a retention spring;
      a topside arm having a curved shape along a length of the topside arm such that an end of the topside arm is bent toward the retention spring; and
      a pivot ring connecting the retention spring to the topside arm; and
   a lockarm pivotally engaged with the retention arm, including:
      an attachment portion having a pivot bar configured to be received in the pivot ring of the retention arm;
      a strut portion connected to the attachment portion; and
      a clasp portion having an opening including a clasp lock, at least one protrusion, and an unlocking slot disposed at an end of the opening, wherein the clasp lock has a first width and is configured to engage a chokebox stem of the bracket and wherein the unlocking slot has a second width narrower than the first width.

5. The self-ligating insert and bracket of claim 4, wherein an angle of the edgewise slot with respect to a vector normal to a surface of the pad is approximately 50 degrees.

6. The self-ligating insert and bracket of claim 4, wherein the bracket further comprises a gingival slot disposed under the curved hook stem and configured to receive a gingival archwire.

7. The self-ligating insert and bracket of claim 4 in which the chokebox stem includes perpendicular projections on opposite lateral sides and the clasp lock engages the chokebox stem beneath the projections.

8. An orthodontic system, comprising:
   a self-ligating insert; and
   a bracket including:
      a pad; and
      a body disposed on the pad, including:
         a curved hook stem extending from the body;
         a gingival hook disposed at an end of the curved hook stem;
         a chokebox stem disposed between the curved hook stem and the body;
         a topside head disposed at an incisal end of the body;
         a retention groove disposed in the body and comprising:
            an incisal opening having a first cross-sectional area;
            a gingival opening having a second cross-sectional area; and
            a pressure point between the incisal opening and the gingival opening such that the retention groove has a third cross-sectional area, wherein the third cross-sectional area is smaller than the first and second cross-sectional areas;
         an edgewise slot disposed in the body and configured to receive an edgewise archwire; and
         an occlusal slot disposed under the topside head and configured to receive an occlusal archwire,
      wherein the retention groove of the bracket is configured to receive a first portion of the self-ligating insert and the chokebox stem is configured to receive a second portion of the self-ligating insert.

9. The system of claim 8, wherein the bracket further comprises a gingival slot disposed under the curved hook stem and configured to receive a gingival archwire.

10. The system of claim 8, wherein the self-ligating insert comprises:
    a retention arm, including:
       a retention spring;
       a topside arm; and
       a pivot ring connecting the retention spring to the topside arm; and
    a lockarm pivotally engaged with the retention arm, including:
       an attachment portion having a pivot bar configured to be received in the pivot ring of the retention arm;
       a strut portion connected to the attachment portion; and
       a clasp portion having a clasp lock and an unlocking opening, wherein the clasp lock is configured to engage the chokebox stem of the bracket.

11. The system of claim 10 in which the chokebox stem includes perpendicular projections on opposite lateral sides and the clasp lock engages the chokebox stem beneath the projections.

12. The system of claim 10, wherein the pivot bar has a round cross-section and is molded with the lockarm.

13. An orthodontic system, comprising:
    a self-ligating insert; and
    a bracket including:
       a pad; and
       a body disposed on the pad, including:
          a curved hook stem extending from the body;
          a gingival hook disposed at an end of the curved hook stem;
          a chokebox stem disposed between the curved hook stem and the body;
          a topside head disposed at an incisal end of the body;
          a retention groove disposed in the body and comprising:
             an incisal opening having a first cross-sectional area;
             a gingival opening having a second cross-sectional area; and
             a pressure point between the incisal opening and the gingival opening having a third cross-sectional area, wherein the third cross-sectional area is smaller than the first and second cross-sectional areas;
an edgewise slot disposed in the body and configured to receive an edgewise archwire; and
an occlusal slot disposed under the topside head and configured to receive an occlusal archwire,
wherein the retention groove of the bracket is configured to receive a first portion of the self-ligating insert and the chokebox stem is configured to receive a second portion of the self-ligating insert;
wherein the self-ligating insert comprises:
a retention arm, including:
a retention spring;
a topside arm; and
a pivot ring connecting the retention spring to the topside arm; and
a lockarm pivotally engaged with the retention arm, including:
an attachment portion having a pivot bar configured to be received in the pivot ring of the retention arm;
a strut portion connected to the attachment portion; and
a clasp portion having a clasp lock and an unlocking opening, wherein the clasp lock is configured to engage the chokebox stem of the bracket;
wherein the topside arm has a curved shape along a length of the topside arm to engage the pressure point in the retention groove and the topside arm comprises a release lock disposed at an end portion of the topside arm, the release lock configured to engage with a wall of the retention groove when the retention aim is partially withdrawn from the bracket.

14. The system of claim 13 in which the chokebox stem includes perpendicular projections on opposite lateral sides and the clasp lock engages the chokebox stem beneath the projections.

* * * * *

UNITED STATES PATENT AND TRADEMARK OFFICE
CERTIFICATE OF CORRECTION

| | | |
|---|---|---|
| PATENT NO. | : 7,828,549 B1 | Page 1 of 1 |
| APPLICATION NO. | : 12/256859 | |
| DATED | : November 9, 2010 | |
| INVENTOR(S) | : Alexander J. Wildman | |

It is certified that error appears in the above-identified patent and that said Letters Patent is hereby corrected as shown below:

Column 3, line 5, "Teppler" should read --Tepper--;

Column 14, line 12, "aim" should read --arm--.

Signed and Sealed this
Eighth Day of February, 2011

David J. Kappos
*Director of the United States Patent and Trademark Office*